United States Patent [19]

Epstein et al.

[11] Patent Number: 5,759,558
[45] Date of Patent: Jun. 2, 1998

[54] SKIN CARE COMPOSITION

[76] Inventors: Howard Epstein, 34 Chelmsford Rd., Rochester, N.Y. 14618; Matthew S. Jonasse, 16 Orchard Ter., Sodus, N.Y. 14551

[21] Appl. No.: 788,489

[22] Filed: Jan. 28, 1997

Related U.S. Application Data

[63] Continuation of Ser. No. 467,663, Jun. 6, 1995, abandoned, which is a continuation of Ser. No. 391,866, Feb. 22, 1995, abandoned.

[51] Int. Cl.$^6$ .................... A61K 7/00; A61K 7/48
[52] U.S. Cl. .................. 424/401; 514/938; 514/847; 252/304
[58] Field of Search ............ 424/401; 514/937, 514/938, 847; 252/304

[56] References Cited

U.S. PATENT DOCUMENTS

| | | | |
|---|---|---|---|
| 3,879,537 | 4/1975 | Van Scott et al. | 424/311 |
| 3,920,835 | 11/1975 | Van Scott et al. | 424/311 |
| 3,984,566 | 10/1976 | Van Scott et al. | 424/283 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,337,241 | 6/1982 | Ser et al. | 424/59 |
| 4,380,549 | 4/1983 | Van Scott et al. | 424/317 |
| 4,389,418 | 6/1983 | Burton | 424/365 |
| 4,781,918 | 11/1988 | Hofinger et al. | 424/70 |
| 4,879,116 | 11/1989 | Fox et al. | 424/682 |
| 5,013,763 | 5/1991 | Tubesing et al. | 514/772 |
| 5,091,171 | 2/1992 | Yu et al. | 424/642 |
| 5,135,748 | 8/1992 | Ziegler et al. | 424/401 |
| 5,385,938 | 1/1995 | Yu et al. | 514/557 |
| 5,389,677 | 2/1995 | Yu et al. | 514/557 |
| 5,420,106 | 5/1995 | Parab | 514/2 |

FOREIGN PATENT DOCUMENTS

| | | | |
|---|---|---|---|
| 566000 | 10/1987 | Australia | A61K 7/075 |
| 2 599 969 | 12/1987 | France . | |
| 1 492 163 | 3/1974 | Germany | A61K 7/10 |
| 43 42 075 | 6/1994 | Germany | A61K 7/06 |
| 9010429 | 9/1990 | WIPO | A61K 7/06 |

OTHER PUBLICATIONS

The Chemistry and Manufacture of Cosmetics, Second Edition, vol. III, by M.G. deNavarre, Ph. C., B.S., M.S., p. 407, 1941.
Formulations Guide, Carocare Personal Products Chemol, pp. 3,4,6, and 8 (no date available).
Smith,W.P., "Hydroxy Acids and Skin Aging," Cosmetics & Toiletries, vol. 109,pp.41–48(Sep., 1994).

*Primary Examiner*—Sally Gardner-Lane
*Attorney, Agent, or Firm*—Chris P. Konkol

[57] ABSTRACT

The present invention is directed to a method of forming an oil-in-water emulsion containing water-insoluble components, a water-soluble humectant, a weakly acidic component such as an alpha-hydroxy acid and a quaternary ammonium cationic emulsifier. The emulsion is used as a stable skin care cream.

11 Claims, No Drawings

SKIN CARE COMPOSITION

This is a continuation of application Ser. No. 08/467,663 filed on Jun. 6, 1995 now abandoned, which is a continuation of Ser. No. 08/391,866, filed Feb. 22, 1995, now abandoned.

BACKGROUND OF THE INVENTION

This invention relates to improved cosmetic emulsions, especially to emulsions useful for moisturizing and conditioning the skin. This invention more particularly relates to cosmetic compositions using cationic emulsifiers, especially to cosmetically acceptable skin lotions or creams having an emulsified petrolatum or mineral oil base. In distinct embodiments, this invention also relates to methods for preparing skin care compositions emulsified by cationic surfactants and having a petrolatum or mineral oil base.

A normal horny layer of epidermis usually contains 10–20% of moisture which helps to impart elasticity, flexibility, or softness to the skin and to maintain a protective effect for the skin. When the moisture content decreases to less than 10% due to changes in environmental conditions or the like, the skin loses its elasticity and protective function and develops a so-called dry-skin condition which causes various skin problems.

A wide variety of emulsions have been used to moisturize skin. Both oil-in-water (water-out) emulsions and water-in-oil (oil-out) emulsions have been tried. Emulsifiers employed in these formulations have included anionic, nonionic, cationic, and mixtures thereof, although the more common commercial products have used anionic and nonionic emulsifiers.

One skin cream based on cationic emulsifiers that has been popular with consumers is CUREL lotion sold by Bausch & Lomb Incorporated. The product is a skin care composition which uses a quaternary ammonium compound as the sole emulsifying agent in an oil-in-water emulsion. By using particular quaternary ammonium compounds, superior properties for a hand care product result. Cosmetically acceptable products can be prepared, including a substantial quantity of petrolatum or mineral oil, in combination with fatty alcohols and fatty ester emollients. The composition has excellent tactile properties and, at the same time, provides good protection to the hands of the user. See U.S. Pat. No. 4,389,418.

Other skin care products using cationic surfactants are described in U.S. Pat. Nos. 4,781,918, 5,013,763, and 5,135,748.

Hydroxy (alpha and beta), keto, carboxylic, and dicarboxylic acids have long been used in a wide variety of retail cosmetic products to remove dead cells from the surface of the skin and to assist moisturization, thus providing a clearer and more beautiful complexion. See U.S. Pat. Nos. 3,879,537, 3,920,835, 3,984,566, 4,105,783, 4,197,316, 4,234,599, 4,380,549, and 5,691,171. Also see Smith, W. P., "Hydroxy Acids and Skin Aging," Cosmetics & Toiletries, Vol. 109, pp. 41–48 (September, 1994). They are components of interest in current cosmetic products because of the demand for products that diminish the appearance of fine lines on the face and improve the appearance of flaking or dry skin.

Treatments for dry skin often involve the application of hydrocarbons such as petrolatum or mineral oil to cover the skin with a hydrophobic occlusive film which prevents water loss from the skin surface to the environment. Other components such as the hydroxy acids mentioned above and hydrophilic humectants such as polyols, especially glycerin, are included in formulations to add moisture to the skin. It would be desirable to provide more effective formulations which not only prevent water loss from the skin but also act more effectively to directly hydrate dry skin.

SUMMARY OF THE INVENTION

A skin care product exhibiting superior moisturizing properties has now been discovered. The product is an oil-in-water emulsion for topical application which comprises from about 2 to about 10 weight % of a particular cationic emulsifier, about 1 to about 40 weight % of a water-soluble, substantially nonionizable humectant, and a pharmaceutically acceptable, weakly acidic material in an amount sufficient to adjust the pH of the finished emulsion to a value in the range of about 2.5 to about 4.5, preferably 3.0 to 4.0, when the emulsion is diluted with purified water to 10 times its weight. The cationic emulsifier employed in this invention is a quaternary ammonium compound of the formula

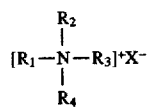

wherein $R_1$ and $R_2$ are each long chain, substantially linear alkyl groups having from about 16 to about 22 carbon atoms, $R_3$ and $R_4$ are each lower alkyl groups having from about 1 to about 3 carbon atoms and X is a salt-forming anion. The humectant is best exemplified by glycerin. The weakly acidic component has a disassociation constant ($pK_a$) within the range of about 1 to about 6. Selection of the weakly acidic component is not believed to be narrowly critical, although alpha hydroxy acids are presently preferred, especially alpha-hydroxy acids of the formula

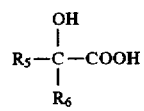

wherein $R_5$ and $R_6$ are aliphatic hydrocarbon and ester groups having 1 to 10 C atoms. Preferred alpha-hydroxy acids are selected from the group consisting of citric acid, glycolic acid, glucuronic acid, galacturonic acid, alpha hydroxybutyric acid, alpha hydroxyisobutyric acid, lactic acid, malic acid, mandelic acid, mucic acid, pyruvic acid, alpha phenylactic acid, alpha phenylpyruvic acid, saccharic acid, tartaric acid, and tartronic acid. Glycolic acid, lactic acid, tartaric acid, and malic acid are particularly preferred.

Although the mechanism by which the emulsion of this invention moisturizes skin is not fully understood, it is presently thought that the unusual effectiveness of the composition is related to the pH and temperature dependent ionization properties of the system. More particularly, it is believed that the temperature change accompanying application of the product to the skin induces a phase change that causes the water-soluble, substantially non-ionizable humectant (e.g., glycerin) to move from the micellular interface (where it associates with the hydrophilic portion of the cationic emulsifier) to the external surface of the emulsion (i.e., to the air/emulsion and skin/emulsion interfaces). The temperature change further ionizes the weakly acidic component, displacing the humectant component associated with the cationic emulsifier at the micellular interface. The result is a formulation having the ability to deliver humectant (e.g., glycerin) to the stratum corneum in amounts beyond that predictable from simple consideration of humectant concentration.

Components in addition to those recited above may be included in the formulation, as will be apparent to those skilled in the art. Discussed in more detail below, examples include petrolatum or mineral oil components, fatty alcohol components, fatty ester emollient components, lubricants such as silicone oils, and preservatives. Being an oil-in-water emulsion, the formulation also includes a significant portion of purified water.

A related, but distinct aspect of the invention relates to the stability of the emulsion. More specifically, it has been found that particularly desirable compositions result if the formulation is prepared in the substantial absence of added salt.

A further, distinct aspect of the invention relates to methods for preparing oil-in-water emulsions of the type exemplified by the formulations of this invention, i.e., formulations containing water-insoluble components, a water-soluble humectant, and a cationic emulsifier. The method comprises:

(a) providing an aqueous solution of a weakly acidic material having a $pK_a$ within the range of about 1 to about 6, said solution having a pH within the range of about 2 to about 4, preferably 3 to 3.8 (as measured at 25° C.);

(b) forming an aqueous mixture of the water-insoluble components and the humectant;

(c) adding the cationic emulsifier to the aqueous mixture at a temperature of about 80° to about 95° C., preferably about 84° to about 88° C., to form a water-in-oil emulsion;

(d) cooling the emulsion formed in step (c) to a temperature within the range from about 45° to about 60° C., preferably about 52° to about 55° C., by the direct injection of purified water, thereby causing a phase inversion and forming an oil-in-water emulsion; and (e) adding said aqueous solution of weakly acidic material at a temperature within the range of about 45° to about 55° C. to the emulsion formed in step (d) to produce an oil-in-water emulsion having a pH within the range of about 2.5 to about 4.5 when diluted with purified water to 10 times its weight.

The method is illustrated and described in more detail in the following description.

DETAILED DESCRIPTION OF THE INVENTION

The quaternary ammonium emulsifiers used in this invention have the general formula:

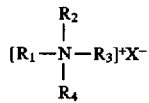

wherein $R_1$ and $R_2$ are each long chain, substantially linear alkyl groups having from about 16 to about 22 carbon atoms, $R_3$ and $R_4$ are each lower alkyl groups having from about 1 to about 3 carbon atoms and X is a salt-forming anion. Preferably the salt-forming anion is chloride, bromide, or iodide. The cationic emulsifiers preferably exhibit hard, waxy and non sticky characteristics. The most preferred cationic emulsifier is dimethyl distearyl ammonium chloride.

The cationic emulsifier is preferably present in the emulsions of this invention in concentrations of about 2 to about 10 weight %, preferably about 3 to 8 weight %.

Humectants act as hygroscopic agents, increasing the amount of water held in the stratum corneum and contributing to the softening of the skin surface. The humectants employed in the formulations of this invention are water-soluble and are substantially nonionizable. By "substantially nonionizable" is meant no significant or detectable disassociation in water. Suitable humectants for the formulations of this invention include glycerin, propylene glycol, sorbitol, polyethylene glycol, 1,2,6-hexanetriol, hydrogenated starch hydrolysate, inositol, mannitol, PEG-5 pentaerythritol ether, polyglyceryl sorbitol, xylitol, sucrose, and the like. Glycerin is a particularly preferred humectant.

The humectant is preferably present in the emulsions of this invention at concentrations of about 1 to about 40 weight %, more preferably about 1 to about 20 weight %, and still more preferably about 5 to about 15 weight %.

Selection of the pharmaceutically acceptable, weakly acidic material employed in this invention is not narrowly critical, so long as the acidic disassociation constant ($pK_a$) is within the range of about 1 to about 6, preferably about 2.5 to about 5.0 (measured at 25° C.). The $pK_a$ of the acidic component is preferably higher than the pH of the finished emulsion. The $pK_a$ is an expression of proton dissociation in solution and is a negative log of the dissociation constant. Therefore, an acid is stronger if its $pK_a$ number is lower. Some acidic materials have more than one proton and therefore have more than one $pK_a$. An example is citric acid which has three protons having acidic dissociation constants as follows: $pK_{a1}=3.13$; $pK_{a2}=4.76$; and $pK_{a3}=6.40$. The acidic material selected will have at least one proton within the desired $pK_a$ range and preferably each of the protons of the acidic material will be within the recited $pK_a$ range.

Examples include hydroxymonocarboxylic acids, hydroxydicarboxylic acids, hydroxytricarboxylic acids, and keto acids. The hydroxy polycarboxylic acids may be provided as the alpha or beta analogs and may be present as free acids, peroxides, lactones, amides, esters, or salts. Illustrative of the variety of acids included are saccharic acid, 2-hydroxyglutaric acid, 3,4-dihydroxyglutamic acid, 2,5-dihydroxy-6-aminohexanoic acid, acetopyruvic acid, acetyl pyruvic acid, beta-floropyruvic acid, tartaric acid, citric acid, 2-hydroxybenzoic acid (salicylic acid), 2-hydroxy-2-methylbutyric acid, 2-hydroxy isobutyric acid, mandelic acid, and 2-hydroxy caproic acid.

One class of preferred acids are hydroxy, dihydroxy, and keto analogs of amino acids. Examples include glycolic acid, lactic acid, pyruvic acid, glyceric acid, malic acid, beta phenyl lactic acid, beta phenyl pyruvic acid, alpha hydroxy isovaleric acid, alpha hydroxy isocaproic acid, 2,3-dihydroxybutanoic acid, and 2,6-dihydroxyhexanoic acid. Preferred acids are selected from the group consisting of citric acid, glycolic acid, glucuronic acid, galacturonic acid, alpha hydroxybutyric acid, alpha hydroxyisobutyric acid, lactic acid, malic acid, mandelic acid, mucic acid, pyruvic acid, alpha phenylactic acid, alpha phenylpyruvic acid, saccharic acid, tartaric acid, tartronic acid, and mixtures thereof.

Another class of preferred acids are described by the general formula:

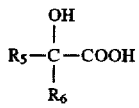

wherein $R_5$ and $R_6$ are aliphatic hydrocarbon and ester groups having 1 to 10 C atoms. Particularly preferred materials within this class are acids selected from the group consisting of glycolic acid, lactic acid, tartaric acid, malic acid, and mixtures thereof. Still more prefered materials within this class are selected from the group consisting of glycolic acid, lactic acid, and mixtures thereof.

It may be that the concentration of cations such as Ca, Fe, K, Na, P, S, and Si effect the ability of the emulsions of this invention to transport moisturizers across the skin membrane. While this phenomena is not understood, the emulsions of this invention will desirably include the following cations (shown as ppm by weight):

Calcium 0.1–14.0
Iron 0.3–3.0
Potassium 0.5–10.0
Sodium 0.5–103.0
Phosphorous 0.9–7.0
Sulfur 0.9–70.0
Silicone 0.3–4.0

The amount of acidic material added to the formulation sufficient to adjust the pH of the finished emulsion to a value in the range of about 2.5 to about 4.5, preferably 3.0 to 4.0, when the emulsion is diluted with purified water to 10 times its weight. The pH is measured at 25° C. In particularly preferred embodiments of this invention the amount of acidic material in the emulsion is within the range from about 0.5 to 7 weight %, more preferably 4 to 6 weight %. This aspect of the invention will illustrated in more detail in the examples and description of the process for preparing the emulsions.

In addition to the cationic surfactant or emulsifier and the alpha-hydroxy acid components, the emulsions of this invention will include other components conventionally used in skin care formulations. Such other components include (a) petrolatum or mineral oil, (b) fatty alcohols, (c) fatty ester emollients, (d) silicone oils or fluids, and (e) preservatives. These components must in general be safe for application to the human skin and must be compatible with the other components of the formulation. Selection of these components is generally within the skill of the art. The following discussion refers to components in the singular although it will be understood that combinations or mixtures are intended to be included as well.

The petrolatum or mineral oil component selected will generally be USP or NF grade. The petrolatum may be white or yellow. The viscosity or consistency grade of petrolatum is not narrowly critical. Petrolatum can be partially replaced with mixtures of hydrocarbon materials which can be formulated to resemble petrolatum in appearance and consistency. For example, mixtures of petrolatum with microcrystalline wax, paraffin wax, and the like may be melted together. Preferred mineral oils are white mineral oils having a viscosity of 6.7 to 69 centistokes at 40° C., a specific gravity (SG 15.6° C./15.6° C.) of 0.828 to 0.890, and a maximum pour point of −18° to −7° C. Still more preferred mineral oils have a viscosity of 6.7 to 17.0 centistokes at 40° C., a specific gravity of 0.828 to 0.860, and a maximum pour point of about −7° to −10° C.

When used the petrolatum or mineral oil component is included in the formulations at a concentration of about 1 to about 10 weight %, more preferably about 2 to about 6 weight %.

Fatty alcohols (typically monohydric alcohols) used in the formulations of this invention stabilize the emulsion and provide a cosmetically acceptable viscosity. Selection of the fatty alcohol is not narrowly critical although $C_{12}$ to $C_{32}$, preferably $C_{14}$ to $C_{22}$, substantially saturated alkanols will generally be employed. Examples include stearyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols.

When used the fatty alcohol is preferably included in the formulations of this invention at a concentration within the range from about 1 to about 8 weight %, more preferably about 2 to about 4 weight %.

Fatty ester emollients enhance the tactile properties of the composition. Examples of suitable fatty esters for use in the formulation of this invention include isopropyl myristate, isopropyl palmitate, isopropyl isostearate, isostearyl isostearate, diisopropyl sebacate, propylene glycol dipelargonate, 2-ethylhexyl isononoate, 2-ethylhexyl stearate, C12–C16 fatty alcohol lactate, isopropyl lanolate, 2-ethyl-hexyl salicylate, and mixtures thereof. The presently preferred fatty ester is isopropyl palmitate.

When used the fatty ester emollient is preferably included in the formulations of this invention at a concentration of about 1 to about 8 weight %, more preferably about 2 to about 5 weight %.

Silicone oils or fluids are used to improve the lubricity of the composition during application to the skin. Preferably the viscosity of the silicone component at a temperature of 25° C. is from about 5 to about 12,500 centistokes. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone—a dimethylpolysiloxane endblocked with trimethyl units—is presently preferred. Dimethicone having a viscosity between 10 and 1000 centistokes is particularly preferred.

When used the silicone oils are preferably included in the formulations of this invention at a concentration of about 0.1 to about 5 weight %, more preferably about 1 to about 2 weight %.

The formulation may also contain other conventional additives employed in cosmetic emulsions. Such additives include aesthetic enhancers, fragrance oils, dyes, preservatives, sun screen additives, and medicaments such as menthol and the like. Preferred aesthetic enhancers are polyquaternium 31 and aluminum starch octenylsuccinate.

Salts are sometimes used to adjust the viscosity of cationic emulsions. However, in a distinct aspect of this invention, it has been found that salt in higher concentrations tends to destabilize the formulations of the present invention. Some salt will be formed during preparation of the emulsion. For example, as discussed in more detail below, it is sometimes desireable to adjust the pH of the weakly acidic material. However, it is preferred that the formulation be prepared in the substantial absence of added salt. The term "added salt" is meant to exclude salts formed as a consequence of adjusting the pH of other components added to the formulation. In more preferred embodiments of this invention, the total salt concentration of the formulation will be no more than 0.5 molar and more preferably is within the range from about 0.1 to about 0.2 molar.

The water employed in the formulations and method of this invention is purified water obtained, e.g., by distilling ordinary tap water, by purifying ordinary water though an ion exchange resin, or by other techniques apparent to those skilled in the art. Water preferably accounts for 30 to 90 weight %, more preferably 55 to 85 weight % of the emulsions of this invention.

The oil-in-water emulsions of this invention are prepared by first forming an aqueous mixture of the water-insoluble components and the humectant. The water-insoluble components include the cationic emulsifier, the petrolatum or mineral oil component, the fatty alcohol component, the fatty ester emollient, and the silicone oil component. The components are preferably added to water in the following sequence: humectant, petrolatum/mineral oil, fatty ester, silicone oil, fatty alcohol. After these components are thoroughly mixed, the cationic emulsifier is added to the aqueous mixture at a temperature of about 80° to 95° C. under agitation to form a water-in-oil emulsion. The input of mixing energy will be high and will be maintained for a time sufficient to form a water-in-oil emulsion having a smooth appearance (indicating the presence of relatively small micelles in the emulsion).

Water is then directly injected into the emulsion to cool it to a temperature of about 45° to about 60° C. The temperature is critical. Unstable emulsions result if the temperature drops below about 45° C. Higher temperatures promote unacceptable water loss through evaporation. During this quench step the emulsion, initially water-in-oil, inverts to form an oil-in-water emulsion.

An aqueous solution of weakly acidic material is then added to the oil-in-water emulsion Attempts to add the acidic material before emulsion formation produced emulsions that were thin and grainy. It is important for emulsion stability that the pH of the solution be within the range of about 2 to 4, preferably 3 to 3.8. It is best not to "shock" the emulsion by addition of more concentrated acids or by variant temperatures. Accordingly the temperature of the acidic solution should be about 45° to about 55° C.

The weakly acidic material is added to the formulation as an aqueous solution having a pH (measured at 25° C.) within the range from about 2 to about 4, preferably about 3.8, according to the method of this invention. Thus it may be necessary to adjust the pH of the acid selected. The pH adjusting agent is not believed to be narrowly critical although agents having weak electronegativities are presently preferred. Examples include amines such as triethanol amine and tetrahydroxypropyl ethylenediamine. Ammonium hydroxide is currently particularly preferred.

After complete mixing and additional cooling, the mixture is filtered to produce a homogeneous lotion or cream.

Water is added at three points during the process: when forming the aqueous mixture of water-insoluble components and humectant; when quenching the water-in-oil emulsion and forming an oil-in-water emulsion, and when the aqueous solution of weakly acidic material is added. The bulk of the water is added during the quench step with minor amounts added with the aqueous mixture of water-insoluble components and humectant and with the weakly acidic material. Preferably, about 20% of the water is added with the aqueous mixture and about 5% is added with the weakly acidic material, with the balance added during quenching.

The invention will now be more fully described and illustrated by the following examples.

EXAMPLE 1

Preparation of Water-In-Oil Phase

The formulation of this Example was prepared in a pilot scale (manufacturer capacity 400 L) Pfaudler mixing tank. This tank is double jacketed, with upper and lower heating/cooling jackets. It has a belt driven 1.5 horsepower agitation motor and is equipped with a single blade S-curved mixer. The tank employs a single non-removable baffle and is equipped with a bottom valve allowing for subsurface addition of materials via a positive displacement pump.

Additionally, all pH measurements on the final product were performed at 25° C. on 1:10 dilutions in purified water.

Initially the Pfaudler tank was charged with 50.0 Kg of purified water. This was agitated and heated to 71°±/5° C. While mixing at a speed of 54 RPMS, 30.0 kilograms(Kg) glycerin 99.5%, 250 grams(g) methyl paraben, 100 g propyl paraben, 10.0 Kg white petrolatum USP, 7.50 Kg isopropyl palmitate and 3.13 Kg dimethicone 10 cst were added in that order. After increasing the temperature to 77° C., 6.250 Kg cetyl alcohol was added and allowed to mix for 10 minutes. While keeping the mixing speed at 54 RPMs and the batch temperature at 77° C., 12.5 Kg of dimethyl distearyl ammonium chloride (Varisoft TA-103 available from Witco Corp., New York, N.Y.) was added. Mixing continued with the temperature raised to 85°-90° C. and the mixing speed increased to 80 RPM until the dimethyl distearyl ammonium chloride was completely dispersed. The heat was then turned off of the tank.

EMAMPLE 2

Preparation of Acidic Material

In a separate carboy, a mixture of 7.15 Kg 70% glycolic acid and 8.83 Kg 88% lactic acid was prepared. To this solution, 2.855 Kg ammonium hydroxide USP was carefully added to achieve a pH of 3.3.

EXAMPLE 3

Preparation of Finished Emulsion

To the oil-in-water phase of example 1, 111.4 Kg of quench water (chilled to 19.8° C. in a Mueller stainless steel 200 L jacketed open top tank) was added over a period of 47 minutes subsurface by the valve in the bottom of the Pfaudler tank. The batch temperature was 46° C. and the mixing speed was reduced to 50 RPM. At this point the acid phase of example 2 was added subsurface to the quench water/emulsion phase over a 30 minute period. When the acid addition was complete, the resulting emulsion was mixed for at least 15 minutes. When the temperature had decreased to 38° C.; the product was finally filtered through a 200 mesh filter screen to a clean holding vessel.

The resulting emulsion was creamy and did not separate over time.

EXAMPLE 4

A dry skin hydration study was performed to compare the moisturizing ability of four lotions containing alpha-hydroxy acids with the moisturizing ability of a lotion noted for its moisturizing ability but not containing any alpha hydroxy acid. The lotions containing alpha hydroxy acids were the lotion of Example 3; Jergens® Advanced Therapy Dual Healing Cream from The Andrew Jergens Co. of Cincinnati, Ohio; EUCERIN® Plus Alphahydroxy Moisturizing Lotion from Beiersdorf Inc. of Norwalk, Conn.; and LUBRIDERM® Moisture Recovery Lotion (containing lactic acid) from Warner-Lambert of Morris Plains, N.J. CUREL® Therapeutic Moisturizing Lotion from Bausch & Lomb Incorporated of Rochester, N.Y. was the lotion not containing alpha hydroxy acids that was compared with the others.

Sixteen female panelists between the ages of 25 and 60 years completed the study. At the time of the study all were in relatively good health and had a dry skin score of at least Grade 2 when examined using the following grading scale:

0=Smooth, no evidence of dryness

1=Slightly dry skin

2=Moderately dry skin, flaking, peeling

3=Severely dry skin, flaking, peeling

The panelists refrained from using moisturizers, creams, lotions, and sunscreen products on their legs for one week before the start of the study and also refrained from shaving their legs 72 hours before the start of the study. Ivory soap was used by all panelists during the study and for five days prior to the study.

Four pairs of treatment sites were rotated between areas on each panelist's legs (outer aspect of the calf). Each of these areas was split into two treatment sites. One site received Curel as described below and the other site received one of the four alpha hydroxy acid products. The designated test sites (each measuring 2.5 cm.×2.5 cm.) was treated using a dose of 2 mg/cm$^2$ of the test material applied by a 0.5 cc syringe and spread over the test area using a finger cot. Each panelist received all test materials. A fifth site on each leg was maintained as an untreated control site.

Skin moisture levels were tested with a NOVA DPM 9003 instrument which measures capacitance on the skin surface. Electrical capacitance of the skin surface has been shown to be related to stratum corneum water content. Tagami, H., "Impedance Measurement for Evaluation of the Hydration State of the Skin Surface," *Cutaneous Investigation in Health and Disease*, pp. 79–111, Marcel Dekker, Inc (New York, N.Y., 1989) and Dikstein, S., et al., "Comparison of Different Instruments for Meqasuring Stratum Corneum Moisture Content," *International Journal of Cosmetic Science*, Vol. 8, pp. 289–292 (1986).

Prior to the study, the test materials were applied to an area of a glass slide measuring 2.5 cm.×2.5 cm. using a finger cot. After a 30 minute drying time, capacitance measurements were taken with the NOVA instrument in five minute intervals until the readings were zero. If the values were not zero after a 30-minute drying time for any product, the additional time required to reach a zero reading was added to the 30 minute time prior to the first post-treatment reading. This was done to ensure that the skin capacitance measurements on the panelists were not influenced by unevaporated water or other components of the test materials.

Panelists remained in a room with a temperature of 20°–25° C. and a relative humidity of 30–40% during the study. After a 30-minute equilibration period, transepidermal water loss measurements were taken at the untreated control site every 5 minutes until the assessments were consistent. After consistent values were obtained, baseline measurements were taken at all sites using both instruments. The test materials were then applied to the appropriate test sites as described above. Measurements were taken in triplicate at 60, 90, 120, 180, and 240 minutes to determine the effect of the test products on skin moisturization. The mean of the three readings was used in subsequent analysis.

Repeated measures analysis of variance (ANOVA) techniques were used to determine the existence, if any, of significant differences between the treatment pairs. This design also evaluated the effect of time as well as the potential for interaction between sample and time. All hypothesis testing was performed at the alpha=0.05 level. Results of the NOVA instrument measurements (reported as capacitance in pico Farads) are shown in Tables 1–4 below.

Table 1 shows the lotion of Example 3 compared with CUREL Therapeutic Moisturizing Lotion. The sites treated with the lotion of Example 3 exhibited greater skin moisture content then CUREL lotion at each time point.

TABLE 1

| | Minutes After Application | | | | |
|---|---|---|---|---|---|
| | 60 | 90 | 120 | 180 | 240 |
| CUREL lotion | 241.9 | 240.4 | 247.0 | 250.5 | 246.1 |
| Example 3 | 333.8 | 306.8 | 301.8 | 296.1 | 289.9 |

Table 2 shows JERGENS Advance Dual Healing Lotion compared with CUREL Therapeutic Moisturizing Lotion. The sites treated with the JERGENS lotion exhibited greater skin moisture content than the sites treated with CUREL at the 60-minute time point, but the lotions performed similarly at the other time points.

TABLE 2

| | Minutes After Application | | | | |
|---|---|---|---|---|---|
| | 60 | 90 | 120 | 180 | 240 |
| CUREL lotion | 234.5 | 226.3 | 239.4 | 232.5 | 231.7 |
| JERGENS lotion | 291.1 | 245.0 | 245.4 | 231.3 | 229.0 |

Table 3 shows EURCERIN Plus Alphahydroxy Moisturizing Lotion compared with CUREL Therapeutic Moisturing Lotion. The sites treated with EURCERIN lotion exhibited greater skin moisture content than the sites treated with CUREL at each time point.

TABLE 3

| | Minutes After Application | | | | |
|---|---|---|---|---|---|
| | 66 | 90 | 120 | 180 | 240 |
| CUREL lotion | 250.6 | 221.8 | 232.8 | 229.2 | 240.8 |
| EUCERIN lotion | 330.3 | 279.6 | 276.0 | 262.0 | 268.8 |

Table 4 showns LUBRIDERM Moisture Recovery Lotion compared with CUREL Therapeutic Moisturizing Lotion. The sites treated with CUREL lotion exhibited greater skin moisture than the sites treated with LUBRIDERM lotion at all time points except the 60-minute point.

TABLE 4

| | Minutes After Application | | | | |
|---|---|---|---|---|---|
| | 60 | 90 | 120 | 180 | 240 |
| CUREL lotion | 255.9 | 249.8 | 259.9 | 260.6 | 251.2 |
| LUBRIDERM lotion | 276.5 | 225.0 | 214.7 | 202.8 | 194.3 |

What is claimed:

1. A method for preparing an oil-in-water emulsion containing water-insoluble components, about 5 to about 40 weight % of a water-soluble, substantially non-ionizable humectant, and from about 3 to about 10 weight % of a quaternary ammonium cationic emulsifier, which method comprises:

(a) providing an aqueous solution of an alpha hydroxy acid having a $pK_a$ within the range of about 1 to about 6, said solution having a pH within the range of about 2 to about 4;

(b) forming an aqueous mixture of the water-insoluble components and the humectant;

(c) adding the cationic emulsifier to the aqueous mixture at a temperature of about 80° to about 950° C. to form a water-in-oil emulsion;

(d) cooling the emulsion formed in step (c) to a temperature within the range from about 45° to about 600° C. by the direct injection of purified water, thereby causing a phase inversion and forming an oil-in-water emulsion; and (e) adding said aqueous solution of alpha hydroxy acid at a temperature within the range of about 45° to about 55° C. to the emulsion formed in step (d) to produce an oil-in-water emulsion having a pH within the range of about 2.5 to about 4.5 when diluted with purified water to 10 times its weight.

2. The method of claim 1 wherein the aqueous solution provided in step (a) has a pH within the range of about 3 to about 3.8.

3. The method of claim 1 wherein the cationic emulsifier is added to the aqueous mixture at a temperature of about 84° to about 88° C.

4. The method of claim 1 wherein the emulsion formed in step (c) is cooled to a temperature within the range from about 52° to about 55° C.

5. A method for preparing an oil-in-water emulsion containing water-insoluble components, a water-soluble humectant, and a cationic emulsifier, which method comprises:

(a) providing an aqueous solution of a weakly acidic material having a $pK_a$ within the range of about 1 to about 6, said solution having a pH within the range of about 2 to about 4, wherein the weakly acidic material is selected from the group consisting of hydroxymonocarboxylic acids and hydroxypolycarboxylic acids; keto acids; and hydroxy, dihydroxy, and keto analogs of amino acids;

(b) forming an aqueous mixture of the water-insoluble components and from about 5 to about 40 weight percent of a water-soluble, substantially nonionizable humectant;

(c) adding the cationic emulsifier to the aqueous mixture at a temperature of about 80° to about 950° C. to form a water-in-oil emulsion, wherein the cationic emulsifier comprises from about 3 to about 10 weight % of a quaternary ammonium compound having the formula

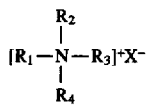

wherein $R_1$ and $R_2$ are each long chain, substantially linear alkyl groups having from about 16 to about 22 carbon atoms, $R_3$ and $R_4$ are each lower alkyl groups having from about 1 to about 3 carbon atoms and X is a salt-forming anion;

(d) cooling the emulsion formed in step (c) to a temperature within the range from about 45° to about 60° C. by the direct injection of purified water, thereby causing a phase inversion and forming an oil-in-water emulsion; and (e) adding said aqueous solution of alpha hydroxy acid at a temperature within the range of about 45° to about 55° C. to the emulsion formed in step (d) to produce an oil-in-water emulsion having a pH within the range of about 2.5 to about 4.5 when diluted with purified water to 10 times its weight.

6. The method composition of claim 5, wherein the weakly acid material is selected from the group consisting of hydroxymonocarboxylic acids, hydroxydicarboxylic acids, and hydroxytricarboxylic acids, and keto acids.

7. The method of claim 5 wherein the humectant is selected from the group consisting of propylene glycol, polyethylene glycol, sorbitol, and glycerin.

8. The composition of claim 5 wherein the humectant is glycerin.

9. The composition of claim 5 wherein the weakly acidic material is an alpha hydroxy acid described by the formula

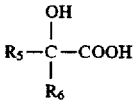

wherein $R_5$ and $R_6$ are aliphatic hydrocarbon and ester groups having 1 to 10 C atoms.

10. The composition of claim 9 wherein the alpha hydroxy acid is selected from the group consisting of citric acid, glycolic acid, glucuronic acid, galacturonic acid, alpha hydroxybutyric acid, alpha hydroxyisobutyric acid, lactic acid, malic acid, mandelic acid, mucic acid, pyruvic acid, alpha phenylactic acid, alpha phenylpyruvic acid, saccharic acid, tartaric acid, tartronic acid, and mixtures thereof.

11. The composition of claim 10 wherein the alpha hydroxy acid is selected from the group consisting of glycolic acid, lactic acid, tartaric acid, malic acid, and mixtures thereof.

* * * * *